(12) United States Patent
Sokolov et al.

(10) Patent No.: US 9,417,170 B2
(45) Date of Patent: Aug. 16, 2016

(54) HIGH RESOLUTION, HIGH SPEED MULTI-FREQUENCY DYNAMIC STUDY OF VISCO-ELASTIC PROPERITES

(75) Inventors: Igor Sokolov, Potsdam, NY (US); Maxim Evgenevich Dokukin, Potsdam, NY (US)

(73) Assignee: CLARKSON UNIVERSITY, Potsdam, NY (US)

( * ) Notice: Subject to any disclaimer, the term of this patent is extended or adjusted under 35 U.S.C. 154(b) by 827 days.

(21) Appl. No.: 13/550,344

(22) Filed: Jul. 16, 2012

(65) Prior Publication Data

US 2013/0018623 A1    Jan. 17, 2013

Related U.S. Application Data

(60) Provisional application No. 61/508,279, filed on Jul. 15, 2011.

(51) Int. Cl.
*G01L 25/00* (2006.01)
*G01N 3/32* (2006.01)

(52) U.S. Cl.
CPC .......... *G01N 3/32* (2013.01); *G01N 2203/0094* (2013.01); *G01N 2203/0218* (2013.01)

(58) Field of Classification Search
CPC ...................................................... G01N 3/32
USPC ........................................................ 702/113
See application file for complete search history.

(56) References Cited

U.S. PATENT DOCUMENTS

| 7,605,368 | B2* | 10/2009 | Shigeno et al. ............... 250/306 |
| 8,646,109 | B2* | 2/2014 | Hu et al. ........................... 850/1 |
| 2006/0000263 | A1* | 1/2006 | Su et al. .......................... 73/105 |
| 2007/0012093 | A1* | 1/2007 | Kwon et al. .................... 73/105 |

OTHER PUBLICATIONS

Berdyyeva, T., Woodworth, C., Sovolov, I., Human Epithelial Cells Increase Their Rigidity with Ageing in Vitro: Direct Measurements, Physics in Medicine and Biology, 2005, pp. 81-92, vol. 50.

Binnig, G., Quate, C.F., Gerber, C., Atomic Force Microscope, Physical Review Letters, 1986, pp. 930-933, vol. 56. No. 9.

Garland, J., Pettit, C., Roy, D., Analysis of Experimental Constraints and Variables for Time Resolved Detection of Fourier Transform Electrochemical Impedance Spectra, Electrochimica Acta, 2004, pp. 2623-2635, vol. 49.

Herbert, E., Oliver, W., Pharr, G., Nanoindentation and the Dynamic Characterization of Visoelastic Solids, Journal of Physics D: Applied Physics, 2008, pp. 1-9, vol. 41.

(Continued)

*Primary Examiner* — Tung S Lau
*Assistant Examiner* — Xiuquin Sun
(74) *Attorney, Agent, or Firm* — Bond Schoeneck & King, PLLC; Blaine Bettinger; George McGuire

(57) ABSTRACT

The present invention provides an apparatus and method including hardware and software, which allows collecting and analyzing of data to obtain information about mechanical properties of soft materials. This allows surface mapping of viscoelastic properties in a high-resolution and fast manner. It also allows finding the degree of nonlinearity of the material response of the sample during the measurements. The apparatus can be used as a stand-alone device, or an add-on to either the existing atomic force microscope or nanoindenter device.

17 Claims, 4 Drawing Sheets

(56) References Cited

OTHER PUBLICATIONS

Holly, E., Venkataramen, S., Chambon, F., Winter, H., Fourier Transform Mechanical Spectroscopy of Viscoelastic Materials with Transient Structure, Journal of Non-Newtonian Fluid Mechanics, 1988, pp. 17-26, vol. 27.

Huang, Y., Wen, Y., Curing of Unsaturated Polyester Resins: Effects of Thickening Agent, Polymer, 1994, pp. 5259-5268, vol. 35, No. 24.

In, M., Prud'homme, R., Fourier Transform Mechanical Spectroscopy of the Sol-Gel Transition in Zirconium Alkoxide Ceramic Gels, Rheologica Acta, 1993, pp. 556-565, vol. 32.

Jamison, C., Marangoni, R., Glaser, A., Viscoelastic Properties of Soft Tissue by Discrete Model Characterization, Journal of Engineering for Industry, 1968, pp. 239-247.

Kauppinen, J., Partanen, J., Fourier Transforms in Spectroscopy, 2001.

Malkin, A., On the Optimal Form of a Signal in Fourier Transform Mechanical Spectroscopy, Rheologica Acta, 2004, pp. 1-5, vol. 43.

Oulevey, F., Burnham, N., Gremaud, G., Kulik, A., Pollock, H., Hammiche, A., Reading, M., Song, M., Hourston, D., Dynamic Mechanical Analysis at the Submicron Scale, Polymer Communication, 2000, pp. 3087-3092, vol. 41.

Sahin, O., Magonov, S., Su, C., Quate, C., Solgaard, O., An Atomic Force Microscope Top Designed to Measure Time-Varying Nanomechanical Forces, Nature, 2007, vol. 2.

Sokolov, I., Atomic Force Microscopy in Cancer Cell Research, Cancer Nanotechnology, 2007, pp. 1-17.

Urban, M., McDonald, W., Emission of Acoustic Waves from Polymers Under Stress, American Chemical Society, 1990.

Vanlandingham, M., Villarrubia, J., Recent Progress in Nanoscale Indentation of Polymers Using The AFM, National Institute of Standards and Technology, 2000, pp. 912-915, Jun. 5-8, 2000.

Vanlangidham, N., Villarrubia, J., Guthrie, W., Meyers, G., Nanoindentation of Polymers: An Overview, Macromolecular Symposia, 2001, pp. 15-43, vol. 167.

Wilhelm, M., Reinheimer, P., Ortseifer, M., High Sensitivity Fourier-Transform Rheology, Rheologica Acta, 1999, pp. 349-356, vol. 38.

\* cited by examiner

|  | $E_{bulk}$ MPa | $E'$(10Hz) MPa | $E'$(100Hz) MPa | $E''$(10Hz) MPa | $E''$(100Hz) MPa |
|---|---|---|---|---|---|
| macroDMA | 1.6±0.3 | 2.6±0.6 | 2.9±0.4 | 0.62±0.05 | 1.23±0.05 |
| nanoDMA | 1.5±0.1 | 3.2±0.6 | 4.3±0.4 | 0.32±0.04 | 0.74±0.07 |
| AFM DMA | 1.49±0.08 | 2.4±0.1 | 3.09±0.14 | 0.09±0.01 | 0.64±0.02 |
| AFM FT-DMA | N/A | 2.4±0.1 | 3.10±0.13 | 0.10±0.01 | 0.65±0.03 |

| Property | Prior Art | Present Invention |
|---|---|---|
| Spatial resolution | 20-30 microns | ~200 nm |
| Measurement time at one point | ~100sec (for one frequency) ~250 sec (for 35 frequencies) | ~1-2.5 sec (# of frequencies is virtually unlimited) |
| Detection of non-linearity of stress-strain relation | no | yes |
| Frequency range | 10-300Hz | 10Hz – MHz[*)] |

HIGH RESOLUTION, HIGH SPEED MULTI-FREQUENCY DYNAMIC STUDY OF VISCO-ELASTIC PROPERITES

REFERENCE TO RELATED APPLICATION

The present invention relates to and claims priority to U.S. Provisional Patent Application 61/508,279, filed Jul. 15, 2011, the entirety of which is hereby incorporated by reference. The present invention also relates to Applicant's issued U.S. Pat. No. 7,761,255, issued Jul. 20, 2010, the entirety of which is hereby incorporated by reference.

BACKGROUND

1. Field of Invention

The present invention relates to the study of viscoelastic properties of material at the nanoscale.

2. Background of Art

Viscoelastic properties of materials are currently measured with the help of dynamical mechanical analysis (DMA). DMA machines are dealing with the bulk properties at the macro level. DMA mode is also implemented for several nanoindenters (for example, manufactured by Hysitron (NanoDMA) and Agilent (DCM) http://www.hysitron.com/page_attachments/0000/0629/nanoDMA_Nanoscale_Dynamic_Mechanical_Analysis_for_Viscoelastic_Materials.pdf; http://cp.literature.agilent.com/litweb/pdf/5990-4211EN-.pdf). The claimed ability to measure viscoelastic properties of polymers and biomaterials at the nanoscale might be confusing. While term "nanoscale" means indeed nano for hard materials, it can hardly be applied for soft materials if one is speaking about the lateral resolution.

As an example, using a standard Berkovich probe, a reliable contact can be reached starting from an indentation of ~50-100 nm. This corresponds to the lateral indentation size of a micron. For some soft materials, like PDMS (the Young's modulus is about 0.1-10 MPa), a stable contact can be reached only by using a very dull spherical probe. The lateral resolution in that case could reach tens of microns.

When doing DMA measurements of polymers (polyurethane, polystyrene, PNA, etc.), the fastest time of the measurements is 2-3 minutes per single point of the surface. As previously indicated, soft polymers may not withstand such a long measurement time. Finally, it is unrealistic perform reasonable mapping of a surface. As an example, a rather modest resolution surface map of 128×128 pixels or points (taking an optimistic 2 min per point), would require almost 550 hours or more than 22 days of a continuously running instrument. Due to the time needed, this is impractical.

There are known way to accelerate measurements involving different frequencies. The methods for simultaneous multi-frequency measurements have been previously used to accelerate measurements in electrochemistry (time resolved Fourier transform electrochemical impedance spectroscopy (FT-EIS) (Garland et al., 2004, Popkirov and Schindler, 1993)), infrared (Ferraro and Krishnan, 1990, Urban and Mcdonald, 1990), NMR (Vandenboogaart et al., 1994, Kauppinen and Partanen, 2001) spectroscopy, and in the study of rheology of complex "rheokinetic" liquids (Fourier Transform Mechanical Spectroscopy) (Huang and Wen, 1994, Malkin, 2004, Wilhelm et al., 1999, In and Prud'hornme, 1993, Holly et al., 1988) (Kulichikhin et al., 1984, Malkin, 1987).

Jesse et al. (U.S. Pat. No. 7,775,086) teach the method of bandgap excitation applied to the atomic force microscopy. Multiple frequencies are generated by a pulse-like signal of a finite duration having finite and predefined amplitude and phase spectrum in a given frequency band(s). The amplitudes are significant only in a rather narrow range (band) of frequencies around the chosen one. As a result, the method of Jesse et al. allows obtaining information in the narrow band around the chosen frequencies. All examples taught by Jesse et al. do with relatively high frequency started from 5000 Hz up to several hundreds of KHz.

Sokolov (U.S. Pat. No. 7,761,255) teaches the use of atomic force microscopy method to study dynamic properties of soft materials utilizing simultaneous multi-frequency measurements, and therefore, accelerating the measurements.

A traditional AFM indentation method is based on force and depth curve analysis (Pethica et al., 1983, Oliver and Pethica, 1989, Oulevey et al., 2000a, VanLandingham et al., 2000, VanLandingham et al., 2001, Oliver and Pharr, 2004). An extension of the technique was proposed to measure the frequency specific indentation (Lucas et al., 1997, Oulevey et al., 2000b, Herbert et al., 2008b, Hou et al., 2006) in a regular nanoindentation manner (one frequency at a time). Recently, two new high-resolution high-speed rigidity mapping AFM techniques have been developed by Veeco (HarmoniX™ and PeakForce™) (Sahin et al., 2007). These methods allow measuring rigidity modules, at, for example, 512×512 surface points, as fast as 15-30 min. Both techniques use a rather high operational (single) frequency (tens and hundreds of kHz for HarmoniX and ~1 KHz for PeakForce). The typical range of interesting frequency dependence, however, is substantially lower (10-300 Hz used by Hysitron). Thus, the high-resolution, high-speed, multi-frequency viscoelastic mapping has not been disclosed as of yet.

3. Objects and Advantages

It is a principal object of the present invention to provide an apparatus and method for collecting data and assisting in the performance of high resolution, high-speed, multi-frequency viscoelastic mapping.

Other objects and advantages of the present invention will in part be obvious, and in part appear hereinafter.

SUMMARY OF THE INVENTION

In accordance with the foregoing objects and advantages, the present invention provides

BRIEF DESCRIPTION OF THE DRAWINGS

The present invention will be more fully understood and appreciated by reading the following Detailed Description in conjunction with the accompanying drawings, in which:

FIG. 5 a table comparing parameters using prior art technology and the present invention; and FIG. 6 is a table comparing the moduli of PDMS measured with Macro DMA, nanoindenter DMA, and the present invention's AFM DMA (when the frequencies are sent/measured separately.)

DETAILED DESCRIPTION

Figure 1:
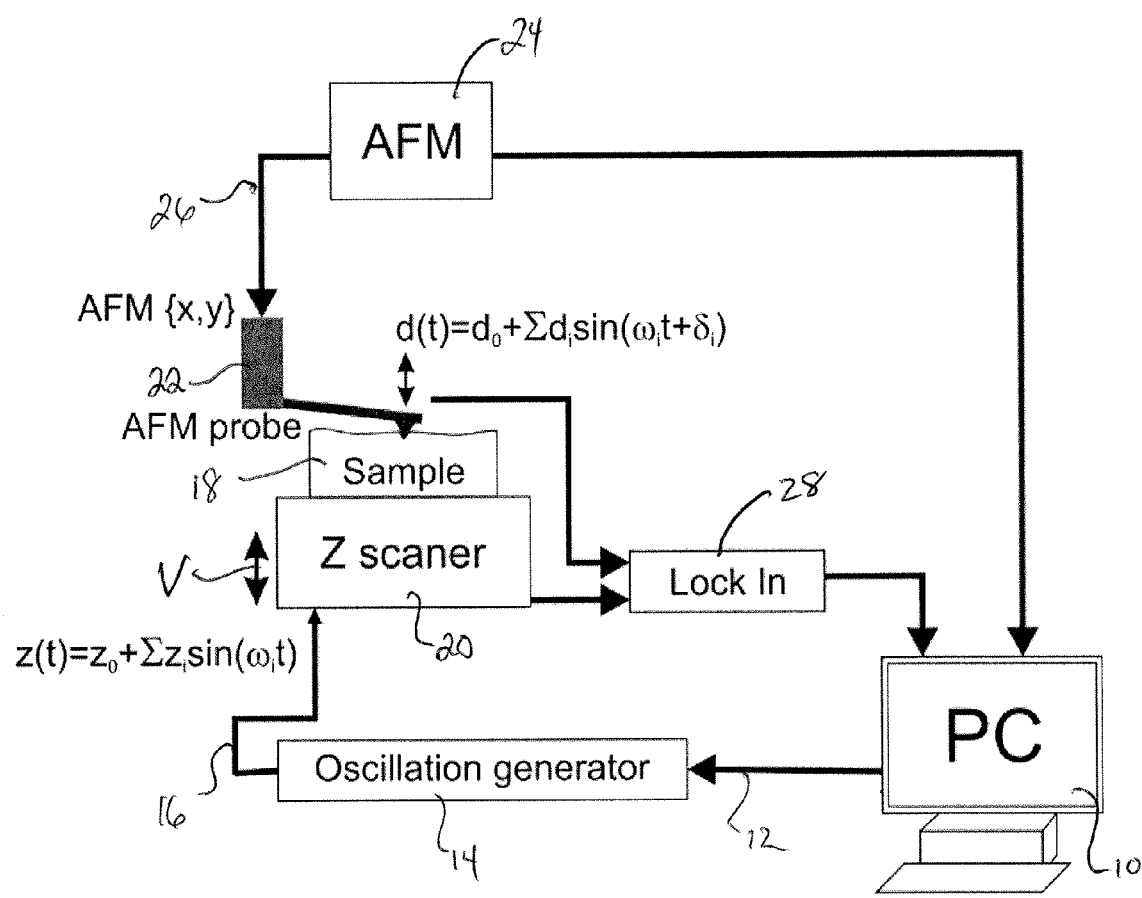
FIG. 1 is a block diagram schematic of an experimental set-up for multi-frequency dynamic measurements of viscoelastic properties of materials.

Embodiments of the invention and the various features and advantageous details thereof are explained more fully with reference to the nonlimiting embodiments that are illustrated in the accompanying drawings and detailed in the following description. Descriptions of well-known starting materials, processing techniques, components and equipment are omitted so as not to unnecessarily obscure the embodiments of the invention in detail. It should be understood, however, that the detailed description and the specific examples, while indicating preferred embodiments of the invention, are given by way of illustration only and not by way of limitation. Various substitutions, modifications, additions and/or rearrangements within the spirit and/or scope of the underlying inventive concept will become apparent to those skilled in the art from this disclosure.

According to an embodiment of the invention, a process comprises: using a computer 10 to send a signal 12 to a signal generator 14 which then generates an oscillatory signal 16 comprising of sum of a predefined number of frequencies; using this signal 16 to generate mechanical oscillations of either the sample surface 18 that is mounted on a Z scanner 20 or to an indenting probe (e.g., photodiode) 22 that is electrically controlled by an atomic force microscope 24 via link 26; recording the mechanical response of the sample surface 18/indenting probe 22 by the software Lock-In amplifier 28 (made on the base of National Instruments ADC card) for the predefined set of frequencies at a particular point, or a number of points over the sample surface; sending the data to computer 10; and analyzing the obtained data using a fast Fourier transform program stored on computer 10 to extract relevant viscoelastic parameters of the sample surface being indented at the said points.

This invention represents a novel approach for high-resolution high-speed nanoindentation, in particular of soft materials. The invention deals with the method and device which are a combination of two previously known technologies/methods: either atomic force microscopy (AFM) or nanoindenter, and the simultaneous measurements of frequency-dependent properties for a predefined set of frequencies. The said device is used to collect the information about the frequency-dependent data at the predefined number of points on the surface, or to do so-called mapping of the surface. The said device provides a high lateral resolution for mapping of the surface mechanical properties of soft material.

The multi-frequency or Fourier transform mechanical spectroscopy is based on processing of a signal which is combined of mechanical oscillations of different frequencies. The input load force comprises of a sum of harmonics of various frequencies. The output signal is processed through the Fourier analyses, so the individual output harmonics can now be analyzed and compared with the input separately for each individual frequency. Comparing the input and output signals with the help of formalism described in the previous section, one can find the parameters characterizing viscoelastic properties of the material. Thus, one can find storage and loss moduli at different frequencies in a single experiment.

An example of mathematical description of the above strategy is as follows. A periodic function $f(t)$ with the period T can be presented as (Holly et al., 1988, Malkin, 2004):

$$f(t) = \frac{a_0}{2} + \sum_{n=1}^{\infty} (a_n \sin n\omega t + b_n \sin n\omega t), \quad (1)$$

where $a_n$ and $b_n$ are amplitudes of higher harmonics of frequencies $n\omega$ and $\omega = 2\pi/T$.

The storage, loss modules, and tangent of the phase shift at a particular frequency $\omega_n = n\omega$ of the viscoelastic material can be found as:

$$E'(\omega_n) = \frac{\tau(\omega_n)}{\varepsilon(\omega_n)} \cos\delta(\omega_n), \ E''(\omega_n) = \frac{\tau(\omega_n)}{\varepsilon(\omega_n)} \sin\delta(\omega_n), \ \tan\delta(\omega_n) = \frac{E'}{E''}, \quad (2)$$

where $\varepsilon(\omega_n)$ and $\tau(\omega_n)$ are the initial signal (strain) and output signal (stress), respectively, $\delta(\omega_n)$ is the phase shift between input and output signals.

When speaking about an indenting probe, eq. (2) can be rewritten in terms of the indenter parameters, similar to eq. (1).

The disclosed here invention deal with a broad excitation range of frequencies. The goal of the disclosed method/apparatus is to measure viscoelastic response of a broad range of frequencies at the same time. It is important that the range of frequencies is broad for the design of the apparatus. The band excitation cannot cover such a broad range of frequencies. Even if the band is made substantially broad, the resulting total amplitude (not the spectral power) of the signal would be too large to be used in the quantitative viscoelastic analysis. The amplitude, for example, can be larger than the initial indentation. As a result, the conduct will be lost under such oscillations. Secondly, in the case of the disclosed here invention, the frequencies can be ranged, for example, from 1 Hz to 10 MHz.

The present invention deals with the acceleration of measurements coming from two sources: 1. Processing of all frequencies at the same time and 2. Not waiting for the relaxation of typically time-dependent contact of the indenter probe with the surface of interest (generally referred as creep). Secondly, the disclosed device and method provide a high lateral resolution when doing mapping of viscoelastic properties of soft materials. Because of not having to wait for the relaxation of the creep, the indenting probe-simple surface contact is substantially smaller than in any typical indenting device. Because the area of the contact defines the resolution of the mapping, the disclosed invention provides high-resolution.

The other embodiment of the invention, a method comprises: a comparison of viscoelastic data measured for two or more predefined frequencies simultaneously with viscoelastic data measured for each of the said frequencies separately; using a computer to perform the analysis of a difference between said two viscoelastic data; the relation of the said difference to possible nonlinear response of the sample material.

The methods for simultaneous multi-frequency measurements have been previously used to accelerate measurements in electrochemistry (time resolved Fourier transform electrochemical impedance spectroscopy (FT-EIS) (Garland et al., 2004, Popkirov and Schindler, 1993)), infrared (Ferraro and Krishnan, 1990, Urban and Mcdonald, 1990), NMR (Vandenboogaart et al., 1994, Kauppinen and Partanen, 2001) spectroscopy, and in the study of rheology of complex "rheokinetic" liquids (Fourier Transform Mechanical Spectroscopy) (Huang and Wen, 1994, Malkin, 2004, Wilhelm et al., 1999, In and Prud'hornme, 1993, Holly et al., 1988) (Kulichikhin et al., 1984, Malkin, 1987). All these methods are based on the assumption of linear superposition of the material response to different frequencies. Obviously this assumption is correct for sufficiently small amplitudes of the oscillations, when the relation between amplitude and measured property is linear. The threshold for nonlinearity has to be defined in each particular application/material. In the case of the material mechanics, starting from some stress/strain threshold (known as the Proportionality limit), the stress/strain relation becomes non-linear (Landau et al., 1986). The moduli of rigidity are defined in the linear regime. The linear superposition of the material response to different loads (included different frequency forces) applied simultaneously is called the Boltzmann superposition principle (Landau et al., 1986).

When doing nanoindentations, it is easy to exceed the stress-stain proportionality limit, which is the major assumption of mechanical models used to extract the rigidity moduli. When dealing with macroscopically homogenous materials, this limit can be found in macroscopic stress-strain tests (for example, stretching or compression). However, for the many materials heterogeneous at the nanoscale it is either difficult or even impossible. For example, when studying the rigidity of biological cells, it is impossible to make a cell of macroscopic size to use in the macroscopic stress-strain tests. (Using an agglomerate of cells, one may obtain an average effective modulus at best, but never the actual modulus distribution over the cell. The same is true for any nanocomposite.)

The disclosed method will allow using the disclosed device to monitor the cross-talking between different frequencies when they are measured simultaneously versus separately. According to the Boltzmann superposition principle (Landau et al., 1986), such a cross-talk is equal to zero (or realistically is rather small) when the response is linear. Its deviation from zero is then be correlated with the non-linearity in stress-stain response.

EXAMPLES

Specific embodiments of the invention will now be further described by the following, nonlimiting example which will serve to illustrate in some detail various features. The following example is included to facilitate an understanding of ways in which an embodiment of the invention may be practiced. It should be appreciated that the examples which follow represent embodiments discovered to function well in the practice of the invention, and thus can be considered to constitute preferred mode(s) for the practice of the embodiments of the invention. However, it should be appreciated that many changes can be made in the exemplary embodiments which are disclosed while still obtaining like or similar result without departing from the spirit and scope of an embodiment of the invention. Accordingly, the examples should not be construed as limiting the scope of the invention.

To demonstrate the principles of work of the disclosed device and method, to estimate the acceleration of measurement time and the increase of lateral resolution, and finally, to test the Boltzmann superposition principle, we describe a simple two-frequency setup shown in FIG. 1. The dynamic mechanical measurements are performed using a piezoelectric scanner/stage 20 (made by NPoint) in combination with DM3100 Veeco AFM 24. The piezoelectric stage 20 is used in the described setup to control the static load and dynamical oscillation during measurements. The AFM detection part is used to measure the force response of the indenting probe. A computer 10 is used to control and measure the probe penetration into the sample surface and to specify the initial static and dynamic displacement/force.

To demonstrate the concept, we use two separate hardware function generators 14 controlled by the computer 10 (this is of course not a scalable approach because it would be unrealistic to put together a 100 of these generators). A sum of two sinusoidal signals produced by these generators together with a DC vertical shift is applied to the Z-piezoelectric stage 20 via line 16. The DC shift is required to provide the needed static load force. Vertical oscillations (represented by line V) of the Z-piezoelectric scanner z(t) and the AFM cantilever response, d(t) (measuring by the AFM photo-detector 22) are directly recorder at 50 kHz using the software Lock-In amplifier 28 made on the base of National Instruments ADC card. The amplitudes of the AFM cantilever $d_i$, the stage $z_i$, and the phase difference between the stage and cantilever oscillations $\delta_i$ are recorded for each frequency created by the oscillation generators. The recorded signal is then analyzed by the FFT (Fast Fourier Transform) method processed by computer 10.

Calculations of Viscoelastic Properties. The AFM probe 22 can be positioned on the sample 18 with nanometer lateral resolution. Amplitudes $d_i$, $z_i$, and $\delta_i$ can be recorded at each point of the surface. Using Equation (3), and definitions of the maximum force amplitude $F_0 = k_{Cant} \Delta z_i$, and the amplitude of sample deformation $X = \Delta z_i - \Delta d_i$, one can find the stiffness k and damping constant C for each particular frequency $\omega_i$:

$$k_{Sample}(\omega_i) = k_{Cant}\left(\frac{\Delta z_i}{\Delta z_i - \Delta d_i}\right)\frac{1}{\sqrt{1+\tan^2\delta_i}} - k_{Cant}, \quad (3)$$

$$C_{Sample}(\omega_i) = \sqrt{\frac{\left(\frac{k_{Cant}\Delta z_i}{\Delta z_i - \Delta d_i}\right)^2 \tan^2\delta_i}{1+\tan^2\delta_i}}\left(\frac{1}{\omega_i}\right)$$

Here it is assumed that the mass of the cantilever is much smaller than the effective oscillating mass of the sample, and that the damping coefficient of the cantilever is equal to 0. While it is true for the AFM cantilever used and for the frequencies considered (below several hundred Hertz), these parameters could be found and taken into account by using a calibration sample of known properties.

Finally, one can find the storage E' and loss E" moduli and the phase $\delta_i$ for each frequency $\omega_i$:

$$E'(\omega_i) = \frac{k_{Sample}(\omega_i)\sqrt{\pi}}{2\sqrt{A_C(d_0)}}, \; E''(\omega_i) = \frac{\omega_i C_{Sample}(\omega_i)\sqrt{\pi}}{2\sqrt{A_C(d_0)}}, \quad (4)$$

$$\tan\delta_i(\omega_i) = \frac{E'(\omega_i)}{E''(\omega_i)}.$$

Here the contact area of the indenting probe $A_C(d_0)$ is measured at the initial (DC) deflection $d_0$. It can be found when the probe geometry is known (it can be found independently with either special grid samples (Berdyyeva et al., 2005) or electron microscopy).

Figure 2:
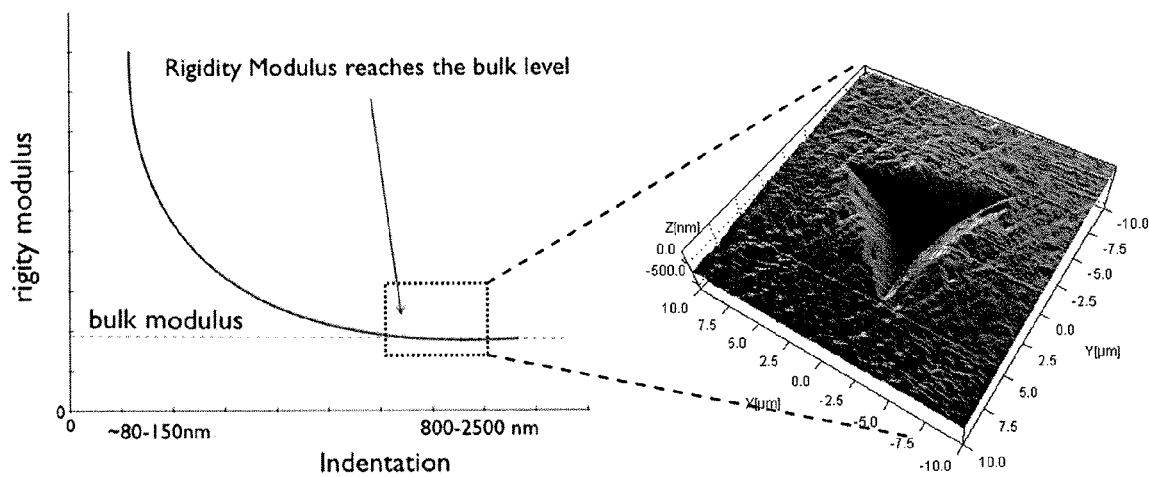
FIG. 2 is a graphical representation of indentation of polyurethane.

High Lateral Resolution: When studying soft materials, existing nanoindenters are no longer "nano" with respect to the spatial resolution, providing the resolution in the micron scale at best (exact resolution depends on the material rigidity). This happens because the probe penetration, and consequently, the probe-surface contact area turns out to be rather large to reliably detect the contact on soft materials. FIG. 2 shows a sketch of indentation of polyurethane by means of Hysitron nanoindenter (TI-950). Using a standard Berkovich probe, a reliable contact can be reached starting from indentation of ~80-150 nm. This corresponds to the lateral indentation size of ~0.6-1 microns. This does not however define the special resolution as of yet. One can see from FIG. 2 that the rigidity modulus decreases with indentation, and reaches its bulk value when the indentation is of the order of ~0.8-2.5 micron (7-12 microns contact area, which is quite far from being "nano"). It is sometimes called "skin effect" (discussion of the nature of this effect is beyond the topic of this proposal). When measuring rigidity, Hysitron, for example, recommends doing it for deeper penetrations to reach constancy of rigidity, where the "skin effect" disappears and the modulus typically reaches its bulk value. When doing DMA, the same initial indentations should be used to avoid the "skin effect". Thus, when comparing the existing and proposed technologies, we consider the penetrations in which the values of rigidity moduli stabilize.

Figure 3:
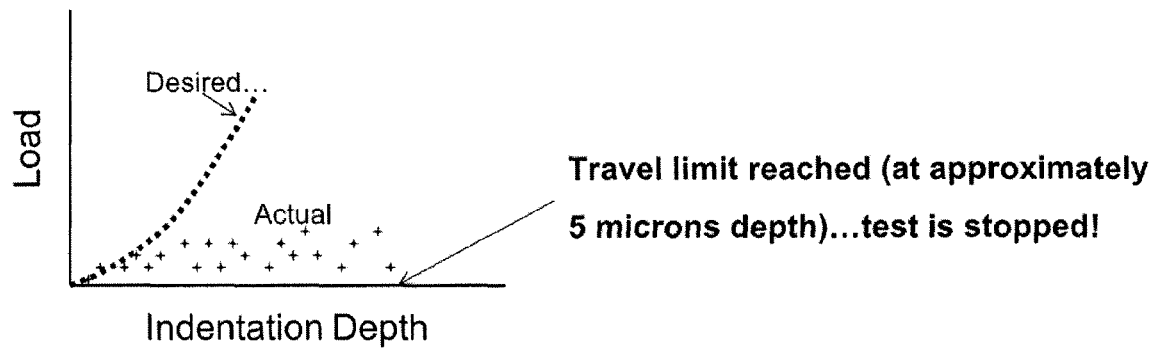
FIG. 3 is a graphical schematic representation of the indentation of a blood clot with a standard Berkovich tip by using a standard nanoindenter.

Impossibility to Measure too Soft Samples by using NANOindenters. When indenting soft materials, deepening of the indenting probe into soft material can be too fast compared to the time of measurement. FIG. 3 shows a schematic of indentation of a blood clot with a standard Berkovich tip by using a standard nanoindenter. (It is certainly a somewhat extreme example. Nevertheless it demonstrates the idea well.) The "desired" load versus indentation curve shown in FIG. 3 is what the instrument records for an "ideal" material response. However, the "actual" curve is unstable. The indentation increases with time and the test stops when the depth reaches its instrumental maximum level (of the order of 5 μm for Hysitron G200 example). One of the possible solutions utilized is to use a rather dull probe of the order of millimeters (http://www.materialstoday.com/webinar/163/tools-techniques-for-nanomechanical-testing-of-biomaterials-part-ii-softer-biomaterial-applications/). Obviously, this can hardly be called "nano".

It has been suggested to attack this problem with a finite element modeling of creep to take it into account (Jamison et al., 1968). However, such an approach is limited to relatively simple materials (in which the structure should be assumed or known in advance).

FIG. 5 demonstrates an example of best values that one can obtain with the benchmark nanoindenter by Hysitron (TI 950) when measuring polydimethylsiloxane resin (PDMS) with the rigidity of 1.5 MPa. One can see that the stable readings of the bulk values of the Young's modulus are obtained when the contact area is 20-30 micron in diameter. Obviously it is far from "nano". The proposed technique demonstrates the ability to obtain the Young's modulus when the probe-sample area is only 200 nm in diameter (see the preliminary results for more detail). This is more than 100 times increase in resolution. Such an improvement in resolution can open a new dimension in the study of mechanical properties of biomaterials and nanocomposites (in which the mechanical properties are strongly dependent on the nanoscale interface).

High Speed of Measurements. The dynamic measurements of soft material with the existing nanoindenters requires several minutes per each point of surface. For example of PDMS, Table 1, such a measurement can take between 100 (for a single frequency) to 250 seconds (for 35 frequencies) per surface point. The proposed technology will require only 1-2.5 seconds per surface point (see the preliminary results for more detail). And due to the parallelism of the frequency measurements of the disclosed method, this particular time does not depend on the number of frequencies used in such a measurement.

This increase in speed will allow studying time-dependent properties of soft materials at the nanoscale. This is important when studying living objects which actively respond to the measurements. For example, biological cells typically respond to the "poking" with AFM probe 22 within a minute (for example, they crawl away and can noticeably change their rigidity). Finally, the fast speed will allow measurements of the mechanics of many soft materials which are impossible to study because of unstable (time-dependent) contact of the indenter probe with the surface of interest (generally referred as creep).

The gain in speed of measurements due to the frequency parallelism allow us simply to avoid a long waiting for creep relaxation because the creep is insignificant when time of contact is sufficiently small. This not only further increases the speed, but also decreases the contact area (spatial resolution) because the probe does not sink too deep in the sample. This effect is stronger when we use AFM as the indenter base because the load forces of AFM is smaller than that of nanoindenters (Binnig et al., 1986) (the smallest force for AFM is ~10 pN versus 20-40 nN for nanoindenters).

Practical Implementation. The disclosed setup can be implemented with a variety of electronic means. Examples can include:

A separate electronics for signal generation and acquisition (may or may not include, for example, FPGA cards). This setup can be used as add-on module for the existing AFM and nanoindenters.

A stand-alone device that will mimic the operations of AFM and/or nanoindenter comprising a) the detection of the probe deflection, b) precise positioning of the probe in the lateral and vertical directions.

Parallel Measurements of Two Frequencies, and the Measurement of Nonlinearity.

In this part of the examples, soft PDMS samples were used. PDMS was chosen due to its softness, durability, and very smooth surface (which allow avoiding problems of roughness). To verify the measurements of viscoelastic properties with the setup described above and sketched in FIG. 1, we did independent measurements using DMA and nanoindenter machines.

DMA Measurements (Done with TA Instruments Q800). The measurements done on a DMA machine on a macroscopic (12 mm) PDMS sample showed the Young's modulus of the material $E_{bulk}$=(1.6±0.3) MPa (it will be called the bulk value). A bit high error obtained can be explained by the difficulty to make flat cylindrical samples. The Proportionality (elastic) limit for the stress was found to be ~0.2 MPa. The storage E' and loss E" moduli were calculated for two frequencies of 10 and 100 Hz (the same frequency will be used for nano indentation of the AFM indenter described here). The results are presented in FIG. 6 ($1^{st}$ row).

Nanoindenter Measurements (Done with TI 950 Hysitron). The nanoindenter measurements on PDMS sample were done with the help of spherical indenter (the radius of curvature is 108 μm). It is worth noting that the use of a sharper Berkowitz probe was not possible as it created the situation described in FIG. 2 (the probe "sinks" in the sample without stopping). The stable rigidity moduli (as recommended by Hysitron procedure) were reached when penetration was ~1000 nm. (DMA measurements were done at that penetration as well, with the amplitude of 10-20 nm). The results are presented in FIG. 6 ($2^{nd}$ row).

AFM measurements with the Disclosed Setup. To verify that the AFM measurements give the value of the rigidity moduli similar to the previous measurements, it was first done sequentially for two frequencies 10 and 100 Hz. The AFM probe geometry was approximately spherical with the radius of curvature of ~120 nm (more precise the geometry was found from the imaging of the inverse to grid sample (Sokolov, 2007)). Both the proportionality limit and the stable values of rigidity moduli reached for the penetrations of ~100-120 nm. The amplitude of oscillation was taken to be 10 nm. The results are presented in FIG. 6 ($3^1$ row). One can see that almost all moduli are rather close to macroDMA and reasonably close to nanoDMA with the exception of the loss moduli (in particular at 10 Hz). (It is not very surprising, however, to see the deviation in the loss moduli, see the explanation of difficulties in their definition in (Herbert et al., 2008a)).

Test of the Boltzmann Superposition Principle in the Disclosed Setup. The Boltzmann superposition principle is our basic assumption allowing use of the Fourier transform multifrequency approach. Therefore, it is important to check its validity. This principle implies that the values of parameters (for example, rigidity moduli) measured at different frequencies simultaneously are the same if they are measured separately (sequentially).

The measurements were done in the same conditions as described above (with the static penetration of 110 nm and the oscillation amplitude of 10 nm). But now both 10 and 100 Hz frequencies were applied simultaneously. The values of the moduli obtained are shown in Table 2 ($4^{th}$ raw). One can see that the Boltzmann superposition principle is valid within the error of measurements. It is worth noting that we do see that the superposition principle breaks if we do the measurements using stresses exceeding the Proportionality (elastic) limit (0.2 MPa stress limit as measured with macroDMA).

Measurement Lateral Resolution. The lateral resolution of the nanoindenter is limited by the area/diameter of the indentation contact. Nanoindenter has the contact diameter of ~20-30 µm when its penetration reaches stable values of the rigidity modulus (close to the bulk value, and the stress under the indenter is within the Proportionality (elastic) limit). The AFM setup described has the contact diameter of ~200 nm under the similar conditions. Thus, one can conclude that the lateral resolution of the described AFM setup can be higher than that for nanoindenter by a factor of >100. The resolution here can be increased even further by the appropriate choice of the size of the indenter (the radius of curvature).

Measurement Time. When doing dynamic (DAM) measurements with nanoindenter, the fastest one can do the measurements is as follows: settling of z motor 60 sec+settling of piezo 40 sec+40 sec measuring/relaxing the creep+initial penetration ~5-10 sec measurements from 15 to 2 sec per frequency. Settling of z motor can be done only once per approach. Thus, the fastest measurements with the settled (z-motor) nanoindenter require from ~1.5 min (single frequency measurement) to >4 min (for 35 frequencies, the number used in nanoDMA).

The measurements with the proposed AFM setup were done within ~1.5-2.5 seconds for both frequencies. The time of measurements is equal to the time of waiting for some creep relaxation (~0.5-1.5 s) and the actual measurement time (~10 periods for the lowest frequency). In principle, the total time can be made even smaller by taken higher lowest frequency. One can see that the time of measurements with the proposed setup can be easily faster than for nanoindenter by a factor of >50 (for single frequency) and >120 (for 35 frequencies). The number of frequencies is limited only by the available electronics, and therefore, cannot be restrictive for the disclosed invention. A particular example is the set of frequencies that are not a multiple of each other. This allows keeping the total signal (the sum of all harmonics) within the limit of electronics. This is convenient but not restrictive.

To amplify, the proposed increase in speed of measurement comes from two factors:

1. Just a straightforward acceleration comes from the execution of different frequencies at the same time.

2. The acceleration due to reason 1 allows doing measurements without long waiting for creep relaxation. Doing sequential frequency measurements, one needs to wait for the creep relaxation to keep the area of contact the same during the measurements (about 2-3 minutes). Otherwise one cannot derive the moduli of rigidity quantitatively. Doing simultaneous multiple frequency measurements, the measurements can be done fast enough (<1 sec). For this measurement time, the contact area will not change substantially even if the creep is not relaxed (in the above example we waited for 1 sec for some creep relaxation, instead of 40 seconds needed for nanoindenter, see the above).

Example of Measurements of Mechanical Properties at Multiple Frequencies Simultaneously Here the measurements done using the disclosed method for 10 frequencies simultaneously are exemplified. This signal consisting of 10 harmonics was applied to a piezoelectric scanner. A sample of PDMS polymer 18 was attached to the scanner 20.

Figure 4:
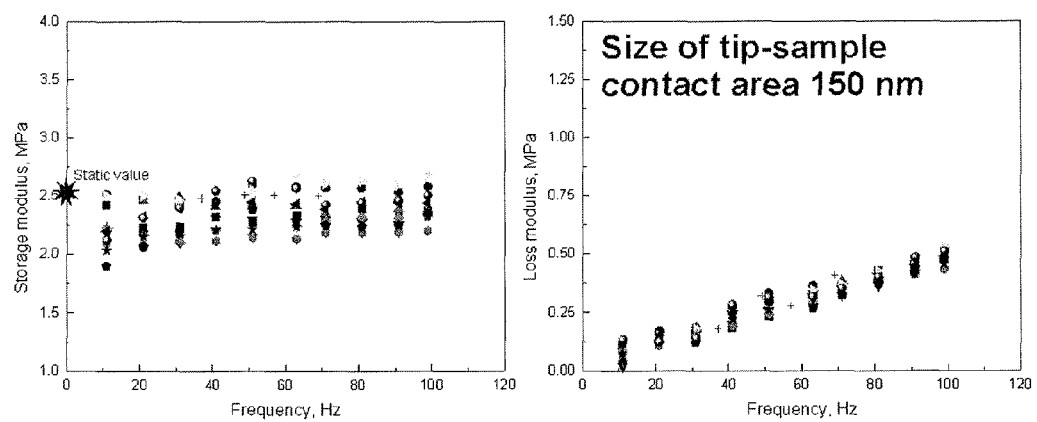
FIG. 4 is a graphical representation of the results of measurements of storage and loss modulus for 10 frequencies measured simultaneously.

FIG. 4 demonstrates the results of measurements of storage and loss modulus for the used 10 frequencies. The total time of measurements was 1.5 seconds. The diameter of the contact between the probe and sample was 150 nm. The measurements were repeated at 10 different locations on the surface of the sample. A static value of the storage modulus is also shown.

Presently, the term "multifrequency AFM" is used for several different techniques: imaging of various harmonics of the AFM cantilever resonances, dual frequency Kelvin force microscopy, and band-excitation AFM. The proposed here combination has no direct relation to those methods. If applied to AFM, the invention can be called "multifrequency force modulation viscoelastic AFM". In the area of spectroscopy, multifrequency approach is called Fourier transform spectroscopy. From that point of view, the said invention could be called "Fourier transform force modulation viscoelastic indentation". Because the dependence of viscoelastic properties on frequency is not called spectroscopy in mechanics, we call it "high-resolution high-speed multifrequency dynamic nanoindentation".

REFERENCES INCORPORATED BY REFERENCE

BERDYYEVA, T. K., WOODWORTH, C. D. & SOKOLOV, I. 2005. Human epithelial cells increase their rigidity with ageing in vitro: direct measurements. Physics in Medicine and Biology, 50, 81-92.

BINNIG, G., QUATE, C. F. & GERBER, C. 1986. Atomic force microscope. Phys. Rev. Lett., 56, 930-933.

FERRARO, J. R. & KRISHNAN, K. 1990. Practical Fourier transform infrared spectroscopy: industrial and laboratory chemical analysis, San Diego, Academic Press.

GARLAND, J. E., PETTIT, C. M. & ROY, D. 2004. Analysis of experimental constraints and variables for time resolved detection of Fourier transform electrochemical impedance spectra. Electrochimica Acta, 49, 2623-2635.

HERBERT, E. G., OLIVER, W. C., LUMSDAINE, A. & PHARR, G. M. 2008a. Nanoindentation and the dynamic characterization of viscoelastic solids. J. Phys. D: Appl. Phys, 41, 074021.

HERBERT, E. G., OLIVER, W. C. & PHARR, G. M. 2008b. Nanoindentation and the dynamic characterization of viscoelastic solids. Journal of Physics D-Applied Physics, 41.

HOLLY, E. E., VENKATARAMAN, S. K., CHAMBON, F. & HENNING WINTER, H. 1988. Fourier transform mechanical spectroscopy of viscoelastic materials with transient structure. Journal of Non-Newtonian Fluid Mechanics, 27, 17-26.

HOU, H. Y., CHANG, N. K. & CHANG, S. H. 2006. Dynamic indentation of polymers using the atomic force microscope. Nanomechanics of Materials and Structures, 171-180.

HTTP://WWW.MATERIALSTODAY.COM/WEBINAR/163/TOOLS-TECHNIQUES-FOR-NANOMECHANICAL-TESTING-OF-BIOMATERIALS-PART-II-SOFTER-BIOMATERIAL-APPLICATIONS/.

HUANG, Y. J. & WEN, Y. S. 1994. Curing of Unsaturated Polyester Resins—Effects of Thickening Agent. Polymer, 35, 5259-5268.

IN, M. & PRUD'HORNME, R. K. 1993. Fourier transform mechanical spectroscopy of the sol-gel transition in zirconium alkoxide ceramic gels. Rheologica Acta, 32, 556-565.

JAMISON, C. E., MARANGONI, R. D. & GLASER, A. A. 1968. Viscoelastic properties of soft tissue by discrete model characterization. Journal of Biomechanics, 1, 33-36, IN5-IN7, 37-46.

KAUPPINEN, J. & PARTANEN, J. 2001. Fourier transforms in spectroscopy, Berlin; N.Y., Wiley-VCH.

KULICHIKHIN, V. G., MALKIN, A. Y. & PAPKOV, S. P. 1984. Rheological properties of liquid crystalline polymer systems. Review. Polymer Science U.S.S.R., 26, 499-524.

LANDAU, L. D., LIFSHI*T*S, E. M., KOSEVICH, A. D. M. & PITAEVSKI*I, L. P. 1986. Theory of elasticity, Oxford Oxfordshire; New York, Pergamon Press.

LUCAS, B. N., OLIVER, W. C. & RAMAMURTHY, A. C. 1997. Spatially resolved mechanical properties of a "TPO" using a frequency specific depth-sensing indentation technique. Antec'97—Plastics Saving Planet Earth, Conference Proceedings, Vols 1 -3, 3445-3449.

MALKIN, A. Y. 1987. Types and mechanisms of non-linearity in the mechanical behaviour of polymers. Polymer Science U.S.S.R., 29, 886-892.

MALKIN, A. Y. 2004. On the optimal form of a signal in Fourier Transform Mechanical Spectroscopy. Rheologica Acta, 43, 1-5.

OLIVER, W. C. & PETHICA, J. B. 1989. Mechanical Characterization Using the Differential Mechanical-Properties Microprobe (Dmpm). Proceedings of the 1989 Sem Spring Conference on Experimental Mechanics, 840-840.

OLIVER, W. C. & PHARR, G. M. 2004. Measurement of hardness and elastic modulus by instrumented indentation: Advances in understanding and refinements to methodology. Journal of Materials Research, 19, 3-20.

OULEVEY, F., BURNHAM, N. A., GREMAUD, G., KULIK, A. J., POLLOCK, H. M., HAMMICHE, A., READING, M., SONG, M. & HOURSTON, D. J. 2000a. Dynamic mechanical analysis at the submicron scale. Polymer, 41, 3087-3092.

OULEVEY, F., GOURDON, D., GREMAUD, G., KULIK, A. J., BURNHAM, N. A. & BENOIT, W. 2000b. Nanoscale study of mechanical properties. Advances in Mechanical Behaviour, Plasticity and Damage, Vols 1 and 2, Proceedings, 917-922.

PETHICA, J. B., HUTCHINGS, R. & OLIVER, W. C. 1983. Hardness measurement at penetration depths as small as 20 nm. Philosophical Magazine A, 48, 593-606.

POPKIROV, G. S. & SCHINDLER, R. N. 1993. Insitu Time-Resolved Impedance Spectroscopy of Processes in the Solid-Liquid Interface—Electropolymerization of Bithiophene. Berichte Der Bunsen-Gesellschaft-Physical Chemistry Chemical Physics, 97, 479-482.

SAHIN, O., MAGONOV, S., SU, C., QUATE, C. F. & SOLGAARD, O. 2007. An atomic force microscope tip designed to measure time-varying nanomechanical forces. Nat Nanotechnol, 2, 507-14.

SOKOLOV, I. 2007. Atomic Force Microscopy in Cancer Cell Research. In: WEBSTER, H. S. N. A. T. (ed.) Cancer Nanotechnology—Nanomaterials for Cancer Diagnosis and Therapy. Los Angeles: APS.

URBAN, M. W. & MCDONALD, W. F. 1990. Emission of Acoustic-Waves from Polymers under Stress—Rheophotoacoustic Fourier-Transform—Ir Spectroscopy. Sound and Vibration Damping with Polymers, 424, 151-163.

VANDENBOOGAART, A., ALAKORPELA, M., JOKISAARI, J. & GRIFFITHS, J. R. 1994. Time and Frequency-Domain Analysis of Nmr Data Compared—an Application to 1d H-1 Spectra of Lipoproteins. Magnetic Resonance in Medicine, 31, 347-358.

VANLANDINGHAM, M., VILLARRUBIA, J. & MEYERS, G. 2000. Recent progress in nanoscale indentation of polymers using the AFM. Proceedings of the Sem Ix International Congress on Experimental Mechanics. Bethel: Soc Experimental Mechanics Inc.

VANLANDINGHAM, M. R., VILLARRUBIA, J. S., GUTHRIE, W. F. & MEYERS, G. F. 2001. Nanoindentation of polymers: An overview. Macromolecular Symposia, 167, 15-43.

WILHELM, M., REINHEIMER, P. & ORTSEIFER, M. 1999. High sensitivity Fourier-transform rheology. Rheologica Acta, 38, 349-356.

What is claimed is:

1. A method for fast, high-resolution mapping of a mechanical property of a viscoelastic surface, the method comprising the steps:

applying an indenting probe to a first indentation depth on the viscoelastic surface;

generating an oscillatory signal comprising the sum of a first set of at least two different predefined frequencies;

generating mechanical oscillations of said viscoelastic surface using said oscillatory signal;

measuring, at said predefined frequencies, a viscoelastic parameter at said first indentation depth, wherein the step of measuring a viscoelastic parameter at said first indentation depth comprises: (i) measuring, at said predefined frequencies, a first viscoelastic parameter at said first indentation depth of said viscoelastic surface, wherein said first viscoelastic parameter is a storage modulus and/or a loss modulus; and (ii) sequentially measuring, for each of said first set of at least two predefined frequencies included in said sum, a second viscoelastic parameter at said first indentation depth of said viscoelastic surface; and analyzing the measurement to determine said property of the viscoelastic surface;

wherein the viscoelastic parameter is measured immediately after applying the indenting probe without waiting for viscoelastic creep relaxation of said viscoelastic surface.

2. The method of claim 1, wherein the generated oscillatory signal is used to generate mechanical oscillations of the indenting probe.

3. The method of claim 1, wherein the step of analyzing the measurement to determine said property of the viscoelastic surface comprises calculating a difference between said first viscoelastic parameter and said second viscoelastic parameter at one of said predefined frequencies, wherein said difference is proportional to the degree of non-linearity of the mechanical response of said viscoelastic surface.

4. The method of claim 1, wherein positioning of said indenting probe is electrically controlled by a controller of an atomic force microscope.

5. The method of claim 1, wherein positioning of said viscoelastic surface is electrically controlled by an external controller.

6. The method of claim 1, wherein the values of said at least two different predefined frequencies are not multiples of each other.

7. The method of claim 1, further comprising the step of measuring said viscoelastic parameter at a second indentation depth.

8. The method of claim 1, further comprising the step of measuring said viscoelastic parameter at a frequency different from said first set of at least two different predefined frequencies.

9. The method of claim 1, wherein said first viscoelastic parameter is selected from the group consisting of viscoelastic creep, non-linearity of the mechanical response of said viscoelastic surface, mathematical functions of storage and/or loss moduli taken at different predefined frequencies and several indentation oscillation amplitudes of said mechanical oscillations, and combinations thereof.

10. The method of claim 1, wherein said first and second viscoelastic parameters of said viscoelastic surface are measured using a nanoindenter or an atomic force microscope.

11. A system for fast, high-resolution mapping of a mechanical property of a viscoelastic surface of a sample, the system comprising:
    a signal generator, said signal generator adapted to generate a first oscillatory signal comprising the sum of a first set of at least two different predefined frequencies, wherein said generated oscillatory signal is transferred to said viscoelastic surface;
    a computer in communication with said signal generator and configured or programmed to send a signal directing said signal generator to generate said oscillatory signal;
    a mechanically oscillating scanner electrically coupled to said signal generator and adapted to have said sample mounted thereon, wherein the mechanically oscillating scanner is adapted to mechanically oscillate according to said generated oscillatory signal;
    a cantilevered probe adapted to engage the viscoelastic surface when said sample is mounted on said mechanically oscillating scanner, wherein said cantilevered probe comprises a position detector configured to detect the position of the cantilevered probe on the viscoelastic surface; and
    a recording unit adapted to measure a viscoelastic parameter of said viscoelastic surface, the recording unit comprising a first input electrically coupled to said scanner, a first output electrically coupled to said scanner, and a second output electrically coupled to the position detector of said cantilevered probe, wherein said first input and said first and second outputs are electrically coupled to said computer;
    wherein said viscoelastic parameter is measured immediately after the cantilevered probe engages the viscoelastic surface, without waiting for viscoelastic creep relaxation of said viscoelastic surface.

12. The system of claim 11, wherein positioning of said cantilevered probe is controlled by an atomic force microscope.

13. The system of claim 11, wherein positioning of said viscoelastic surface is electrically controlled by an external controller.

14. The system of claim 11, wherein said scanner is a piezoelectric scanner.

15. The system of claim 11, wherein said signal generator is further adapted to generate multiple sinusoidal signals together with a DC shift, and transmit said generated DC shift and multiple sinusoidal signals to said scanner.

16. The system of claim 11, wherein the values of said at least two different predefined frequencies are not multiples of each other.

17. The system of claim 11, wherein said first viscoelastic parameter is selected from the group consisting of creep, non-linearity of the mechanical response of said viscoelastic surface, mathematical functions of storage and/or loss moduli taken at different said predefined frequencies and several indentation oscillation amplitudes of said mechanical oscillations, and combinations thereof.

* * * * *